(12) United States Patent
Zoumalan

(10) Patent No.: US 10,893,977 B2
(45) Date of Patent: Jan. 19, 2021

(54) DEVICE AND METHOD TO TREAT EYE CONDITIONS, EYELIDS CONDITIONS, OR BOTH

(71) Applicant: OMERA MEDICAL, INC., Menlo Park, CA (US)

(72) Inventor: Christopher Zoumalan, Los Angeles, CA (US)

(73) Assignee: OMERA MEDICAL, INC., Menlo Park, CA (US)

( * ) Notice: Subject to any disclaimer, the term of this patent is extended or adjusted under 35 U.S.C. 154(b) by 319 days.

(21) Appl. No.: 15/872,909

(22) Filed: Jan. 16, 2018

(65) Prior Publication Data

US 2018/0200106 A1    Jul. 19, 2018

Related U.S. Application Data

(60) Provisional application No. 62/447,397, filed on Jan. 17, 2017.

(51) Int. Cl.
*A61F 9/00* (2006.01)
*A61F 7/00* (2006.01)

(52) U.S. Cl.
CPC .......... *A61F 9/0026* (2013.01); *A61F 7/0085* (2013.01); *A61F 9/0008* (2013.01);
(Continued)

(58) Field of Classification Search
CPC .... A61F 9/0026; A61F 9/0008; A61F 7/0085; A61F 2007/0062; A61F 9/00; A61F 7/00; A61F 2007/0087; A61F 2007/0086; A61F 2007/0096; A61F 2007/0002–0004; A61M 35/003; A61M 11/041; A61H 33/12; A61H 33/06; A61H 33/60; A45D 19/16

See application file for complete search history.

(56) References Cited

U.S. PATENT DOCUMENTS 1,900,201 A    9/1933  Sager
3,749,092 A    7/1973  Williams
(Continued)

FOREIGN PATENT DOCUMENTS

WO    WO-9404116 A1 *  3/1994  ............. A45D 26/00

OTHER PUBLICATIONS

International Search Report and Written Opinion for Application No. PCT/US2018/14013, dated May 29, 2018, 10 pages.

*Primary Examiner* — Tatyana Zalukaeva
*Assistant Examiner* — Heather K Barnwell
(74) *Attorney, Agent, or Firm* — Merchant & Gould P.C.

(57) ABSTRACT

A device for treating eyes, eyelids or both, in the form of a handheld housing is disclosed herein. The device has a first chamber a second chamber acting as a vapor reservoir, and hydrophilic material disposed within the first chamber. The hydrophilic material having has a plurality of pores configured to allow the fluid to seep from the first chamber to the hydrophilic material. A heating element is positioned adjacent the hydrophilic material to convert the fluid to a vapor and continuously regulate a temperature of the vapor. A user interface is disposed on an outside of the housing and configured to control a variable circulator which in turn controls control the temperature of the vapor reaching the user. A method for treating eyes, eyelids, or both is also disclosed.

17 Claims, 11 Drawing Sheets

(52) U.S. Cl.
CPC .............. *A61F 2007/0004* (2013.01); *A61F 2007/0062* (2013.01); *A61F 2007/0086* (2013.01); *A61F 2007/0096* (2013.01)

(56) References Cited

U.S. PATENT DOCUMENTS

| | | | |
|---|---|---|---|
| 3,949,743 A | 4/1976 | Shanbrom | |
| 4,676,237 A * | 6/1987 | Wood | A61M 16/16 128/203.17 |
| 5,010,905 A * | 4/1991 | Snyder | A45D 19/16 132/212 |
| 5,420,961 A | 5/1995 | Walker | |
| 5,531,775 A | 7/1996 | Minoru et al. | |
| 5,588,564 A * | 12/1996 | Hutson | A61F 9/0026 222/383.1 |
| 5,938,693 A * | 8/1999 | Carminucci | A61F 7/0085 607/104 |
| 6,090,085 A * | 7/2000 | Mehl, Sr. | A45D 26/00 601/138 |
| 6,162,046 A | 12/2000 | Young et al. | |
| 6,409,746 B1 | 6/2002 | Igaki et al. | |
| 6,585,509 B2 | 7/2003 | Young et al. | |
| 7,431,570 B2 | 10/2008 | Young et al. | |
| 7,920,777 B2 | 4/2011 | Rabin et al. | |
| 7,942,644 B2 | 5/2011 | Young et al. | |
| 7,981,147 B2 | 7/2011 | Korb et al. | |
| 2003/0055469 A1 | 3/2003 | Ohmura | |
| 2005/0177208 A1 | 8/2005 | Irwin | |
| 2005/0240162 A1 * | 10/2005 | Chen | A61F 9/0026 604/298 |
| 2006/0058714 A1 | 3/2006 | Rhoades | |
| 2006/0116674 A1 | 6/2006 | Goble et al. | |
| 2007/0119969 A1 | 5/2007 | Collins et al. | |
| 2009/0264971 A1 * | 10/2009 | Wickstead | A61F 7/03 607/108 |
| 2010/0010598 A1 | 1/2010 | Igaki | |
| 2011/0133004 A1 | 6/2011 | Thomason et al. | |
| 2012/0310184 A1 | 12/2012 | Pedersen | |
| 2013/0018333 A1 | 1/2013 | Thomason | |
| 2013/0150757 A1 | 6/2013 | Faredoun | |
| 2014/0336565 A1 | 11/2014 | Nichols | |
| 2015/0005750 A1 | 1/2015 | Kelleher et al. | |
| 2015/0043958 A1 * | 2/2015 | Painchaud | B65D 47/2081 401/262 |
| 2016/0324719 A1 | 11/2016 | Badmus et al. | |
| 2017/0136076 A1 | 5/2017 | Soman | |
| 2017/0266457 A1 | 9/2017 | Eckhouse et al. | |
| 2017/0345543 A1 | 11/2017 | Soda | |

* cited by examiner

DEVICE AND METHOD TO TREAT EYE CONDITIONS, EYELIDS CONDITIONS, OR BOTH

CROSS-REFERENCE TO RELATED APPLICATIONS

This application claims the benefit of U.S. Provisional Application No. 62/447,397, entitled Device and Method to Treat Skin and Eye Conditions, filed on Jan. 17, 2017, the entity of which is incorporated herein by reference for all purposes.

FIELD OF THE INVENTION

The present invention relates to a handheld eyelid vaporizer/steamer that delivers aerosolized heat onto the eyelid in order to treat eyelid and eye conditions including chalazions, hordeolums, dry eyes, blepharitis infections, meibomian gland dysfunction, tired eyes and strained eyes. More particularly, the invention relates to a handheld eyelid vaporizer/steamer that uses the physical and therapeutic properties of both steam (gaseous water) and vapor of certain compounds or liquids together with pressure control to treat eye and eyelid disorders.

BACKGROUND OF THE INVENTION

Various eyelid and eye conditions exist which require some variable use of applied heat directly onto the eyelid as a treatment protocol. Direct heat using a warm compress is very popular since they are easily accessible. However, they are limited in success given their short duration of application. For example, repeated heating attempts have to be performed in order to allow the technique to work effectively.

Using steamed water as a source of heat has also been found to be beneficial. The advantages of using steam is that there is no direct contact to the skin, hence a decreased likelihood of a skin burn. The use of steam water has also been advocated, although it is more cumbersome in comparison to the use of warm compresses. The use of heat around the eyelids and eye helps in several ways. For example, applying heat helps open up the eyelid's meibomian glands and to allow the egress of oil glands which may be obstructed or dysfunctional; applying heat also dilates the blood vessels and allows for increased blood flow. The use of applied heat onto the eyelid can help in various disorders such as treating internal or external chalazions or hordeolum (styes), which are blocked eyelid sebaceous oil glands. Other disorders that can benefit from the use of applied heat include dry eye syndrome (DES), blepharitis, meibomitis, allergic conjunctivitis, infections such as preseptal cellulitis, orbital cellulitis, or dacryocystitis, ocular rosacea, contact lens related conjunctivitis or irritation. Tired eyes or eye strain can occur from overuse of eyes, reading, mobile phone use, and can result in dry eyes syndrome or dry eye syndrome-like symptoms.

It has been established that the use of heat can help treat meibomian gland dysfunction. The heat can be placed outside the eyelid or even inside the eyelid. Meibomian gland dysfunction can be associated with various eyelid disorders such as blepharitis, chalazions, hordeolums, and dry eyes. Prior patents have described a heating device with pressure that is placed directly on the eye to treat meibomian gland dysfunction (e.g., U.S. Pat. No. 7,981,147).

Other patents have described treating meibomian gland dysfunction by placing a heating and pressurized system directly on the eye through a scleral lens (lipiflow). The system uses an internal heating system that is not steam or vapor based. The direct heat has been shown to improve the meibomian gland dysfunction in the eyelids but it does not directly treat chalazions or other eyelid disorders. Another method similar to this involves light technology to deliver heat directly onto the eye via a scleral lens to treat meibomian gland disease as well, but it does not directly treat chalazions or other eyelid disorders, for example, ilux (e.g., US20150005750).

However, these past approaches utilize devices that may be uncomfortable, ineffective, clumsy to use, make it difficult to precisely regulate temperature and flow, are not for use with both water and other liquids, and are not comfortable to the eye.

What is needed is a handheld steamer designed specifically for outside of the eyelids.

SUMMARY OF THE INVENTION

To achieve the forgoing and other aspects and in accordance with the purpose of the invention, a steam and/or vapor generator is provided that combines steam and pressure to the user eyelid.

The subject device provides a device for treating eyelid surfaces, eyes, or both, in the form of a handheld housing, the device comprising a first chamber configured as a fluid reservoir; a second chamber opened on a top end of a housing and configured as a steam reservoir; a hydrophilic material disposed within the chamber and configured to connect the chamber, the hydrophilic material having a plurality of pours pores configured to allow the fluid to seep from the first chamber to the hydrophilic material; a heating element positioned adjacent hydrophilic material and the second chamber, the heating element configured to convert the liquid to a vapor and continuously regulate a temperature of the steam; a user interface disposed on an outside of the housing and configured to control a variable circulator, the variable circulator being positioned in an orifice proximate the top end of the housing, the variable circulator functioning to control the temperature of the vapor reaching the user.

In embodiments the device provides a method for treating eyelid surfaces, eyes, or both, the method being performed with a handheld housing, the method comprising filling a first chamber in the housing with a fluid reservoir; connecting a second chamber to the first chamber, the second chamber being configured as a steam reservoir; placing a hydrophilic material within the passage, the hydrophilic material having a plurality of pores; seeping fluid from the first chamber to the hydrophilic material; heating the fluid with a heating element positioned adjacent the hydrophilic material and the second chamber, the heating element configured to convert the liquid to a vapor and continuously regulate a temperature of the steam; toggling a switch to control a variable circulator, the variable circulator being positioned in an orifice at the top end of the housing, the variable circulator functioning to control the temperature of the vapor reaching the user.

The device described herein provides a safe and effective portable treatment for a myriad of eye conditions that utilizes steam and/or vapor, each being readily controlled by the user to ensure effective treatment.

In embodiments, the device provides a plurality of fail-safe mechanisms to avoid injury, while allowing the user to control steam temperature and pressure to maximize results over time.

In embodiments, the steam and vapor flow, and by proxy the temperature, are easily controlled by the user via convenient user interface with multiple buttons for different modes, or a single toggle.

The device provides a mechanism such that the vapor or steam is produced using very low energy thus conserving battery.

The device provides an environment in which microbes are substantially reduced in both the fluid chamber and the vapor/steam chamber.

The device is also is comfortable to use on the eyes.

Further, the device ensures the temperature is within approved ranges for enhanced therapeutic action. A yet further object of the invention is to provide a steamer which supplies moisture-laden air directly to the eye.

Further, the device provides for vapor of distilled water, and also for medicated fluids and the like.

Further, the device provides for a hand-held steamer device having a self-contained easily refillable reservoir.

Further, the device provides a replaceable hydrophilic member that allows fluid seepage to the heating element.

Further, a device that is connected to a mobile application via wireless communication to provide the user the ability to change settings and receive feedback on operation of the device is described.

Further, the device provides a steamer that can treat both the eye and other skin areas and body parts of the user.

Other features, advantages, and aspects of the present invention will become more apparent and be more readily understood from the following detailed description, which should be read in conjunction with the accompanying drawings.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
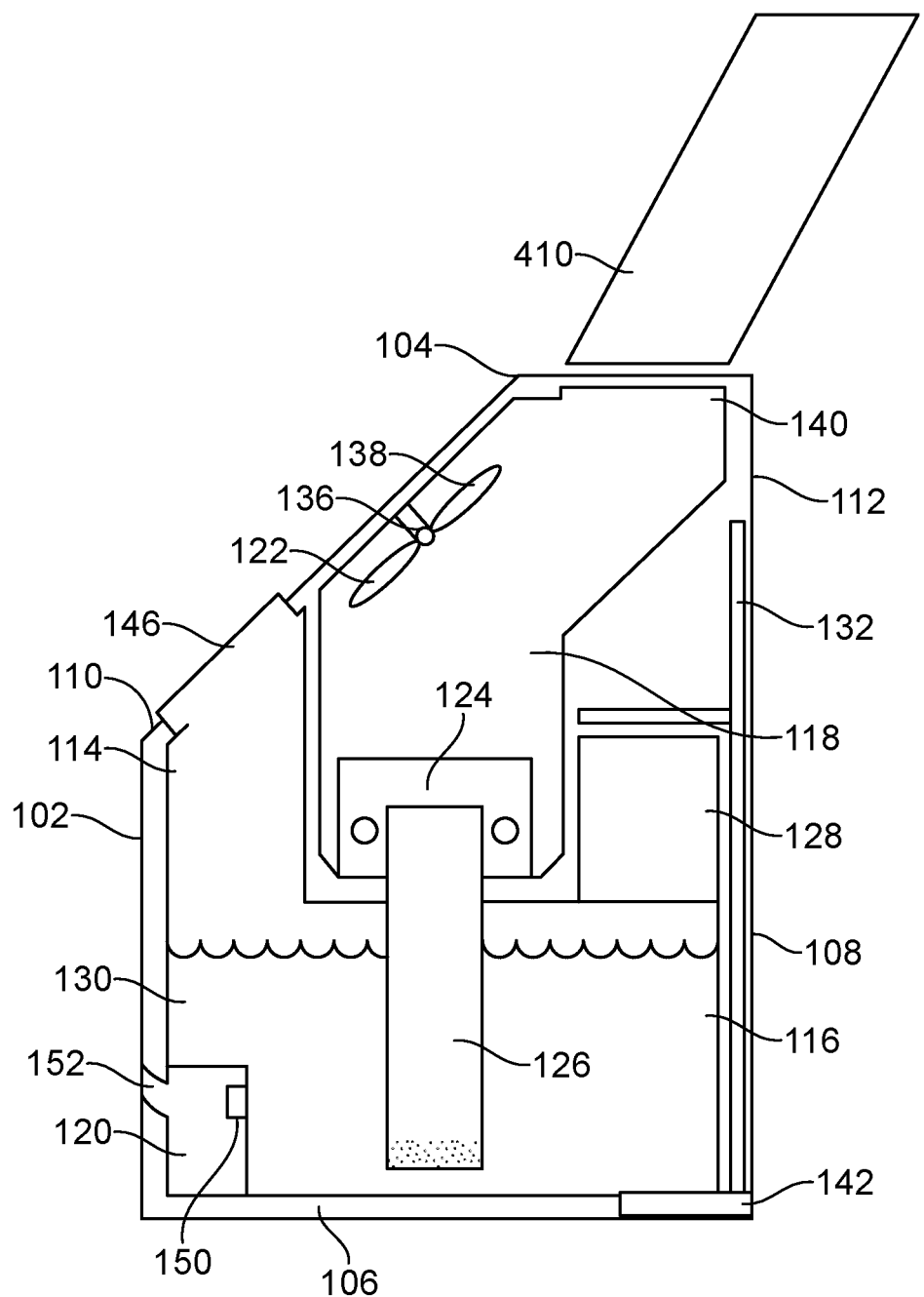
FIG. 1 is a cross-sectional side view of the device in accordance with embodiments of the present invention.

Unless otherwise indicated illustrations in the figures are not necessarily drawn to scale.

DETAILED DESCRIPTION OF THE PREFERRED EMBODIMENTS

The present invention is best understood by reference to the detailed description and examples set forth herein.

Embodiments of the invention are discussed below with reference to the examples. However, those skilled in the art will readily appreciate that the detailed description given herein with respect to these examples is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention.

As used herein, the terms "vapor" and "steam" may be used interchangeably, and refers to: (1) water in the gas phase, which is formed when water boils; and (2) wet steam, which is the visible mist or aerosol of water droplets formed as this water vapor condenses; and/or (3) the vapor or gaseous phase of a fluid or medications.

As used herein, the term "capillary action" (sometimes referred to as also "capillarity" or "capillary motion") is the ability of a liquid or fluid to flow in narrow spaces or pore without the assistance of, or even in opposition to, external forces like gravity.

Referring now to FIG. 1, a vapor device for treating an eyelid, eye or skin surface is shown generally at 100. As an overview, the device comprises a housing 102 having a top 104, a bottom 106, an approximately flat side 108, and a curved, angled, or rounded side 110. It should be appreciated that the housing shape can be of any useful shape, and that the design shown herein is for purposes of example only. The housing 102 is sized in way that makes it portable and comfortable to grasp. The housing 102 has an exterior 112 and an interior 114. The interior 112 is broken down into different chambers: a first chamber 116, a second chamber 118, and a third chamber 120. A heating element 124 is positioned adjacent a hydrophilic element or material 126. A variable circulator 122 is positioned proximate to the top portion 104 of the housing 102, and angled in a parallel to that portion of the housing, but in a manner diagonal or transverse the bottom of the housing 102.

Figure 4:
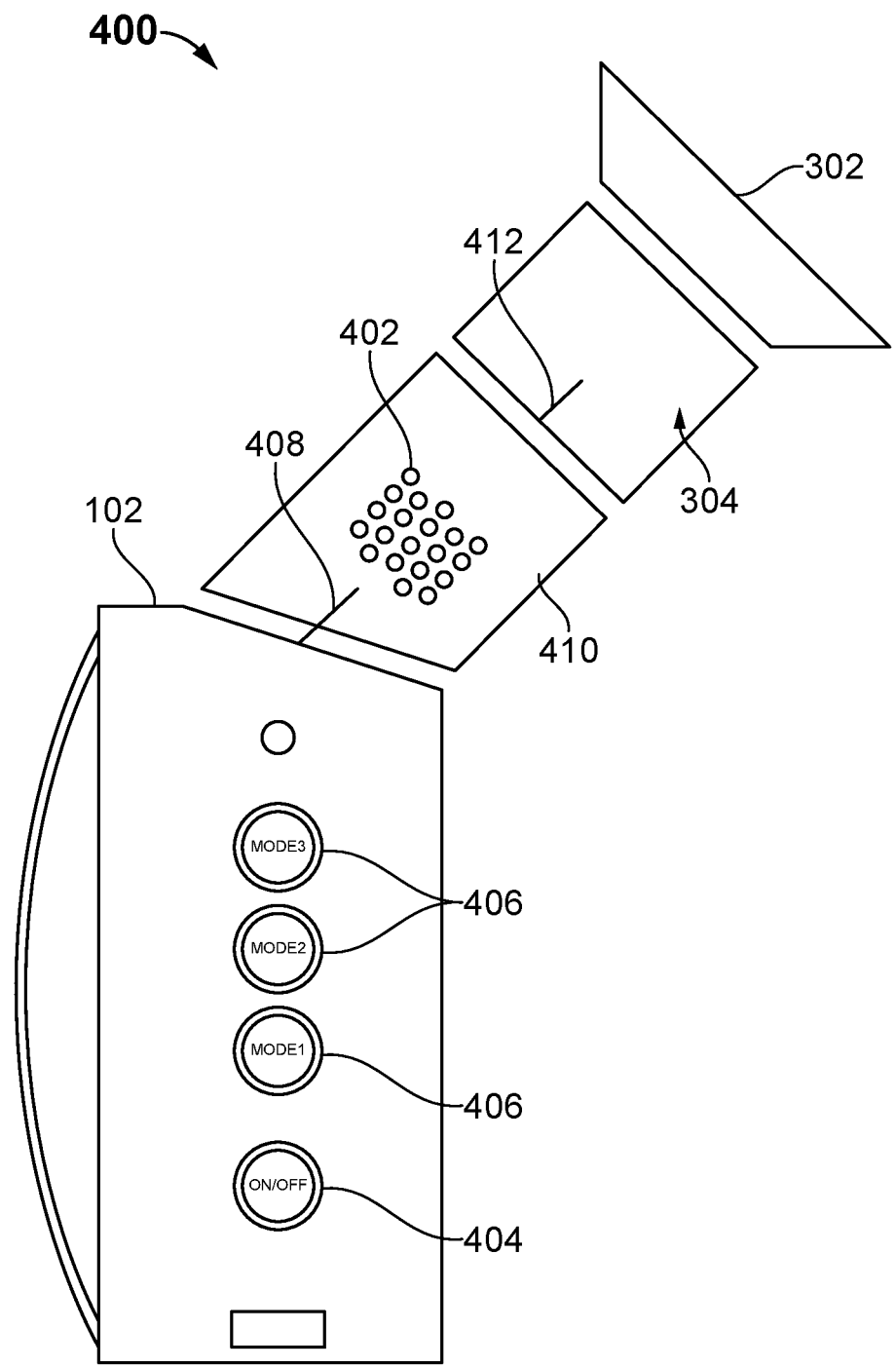
FIG. 4 is a side partially-exploded view of the of the device in accordance with embodiments of the present invention.

More specifically, with reference still to FIG. 1, the housing 102 may be constructed of plastics or other polymers, with a focus on somatosensation and also on the weight of the material. Exemplary materials comprise polyethylene terephthalate (PET or PETE), high-density polyethylene (HDPE), polyvinyl chloride (PVC), low-density polyethylene (LDPE), polypropylene (PP), and polystyrene (PS). Certain rubbers, felts, and cloths may be used to enhance grip and feel as well. In embodiments, the materials shall be biocompatible, electrically safe (including emissions and immunity) and corrosion-resistant. A window, which is shown in greater detail with relation to FIG. 4, provides the user the ability to see the amount of fluid in the chamber (in many cases distilled water). The housing 102 comprises multiple ports for charging a battery, discharging the vapor, steam or mist, and for refilling the chambers. The housing 102, in an embodiment, may be approximately 115 mm wide, 47 mm deep and 24 mm tall. All user contacting materials shall be biocompatible and shall meet applicable requirements of ISO 10993 series of standards. The interior 114 of the housing provides for multiple fluid pathways, electronics gateways, and battery power designed such that the user is not in danger of electric shock.

With reference still to FIG. 1, the first chamber 116 is configured as a fluid reservoir. In some embodiments the fluid 130 is distilled water. In other embodiments, the fluid may be medicated, while in other embodiments, the fluid may be a mixture or combination of distilled water (dH2O) and a medication that is a dissolvable solid or fluid in its own right, this medicated solid of fluid being housed in third chamber 120. The first fluid chamber 116 envelopes the second chamber 118, such that the dH2O fill is approximately or at least 110 ml. In optional embodiments, the first chamber 116 may be modular such that it is removable from the device 100 itself for the user to refill. In exemplary embodiments, the first chamber is refilled through port 146. The first chamber 116 positioned such that it is in fluid communication with a second chamber 118.

Still with reference to FIG. 1, the second chamber 118 is configured as a steam or vapor reservoir. The second chamber 118 is opened at a top end 104 of the housing 102, to form a vapor path, and in some embodiments, may comprise a valve at its top end. The second chamber 118 is positioned on a center-interior portion of the housing 102, and is approximately concentric, but may be any other shape or size. In this way, the first chamber 116 surrounds the second chamber in a shroud like manner. The second chamber 118 may comprise a plurality of sensors, which are discussed in more detail with relation to FIG. 5. The second chamber 118 is in fluid communication with the first chamber 116 via hydrophilic material 126, which is positioned below the second chamber, and within both the first chamber 116 and the second chamber 118. The fluid communication between the chambers is a result of capillary effect, traveling in opposition to external forces (i.e. gravity) up or through the hydrophilic material that is disposed in chambers 116 and 118.

In exemplary embodiments, the hydrophilic material 126 comprises a plurality of pores and allows the fluid from the first chamber to slowly seep into material, where it travels into the second chamber 118 to be converted into vapor or steam, which then rises through the second chamber 118 and through additional elements, to the eye, eyelid or skin of the user. The hydrophilic material 126, as define herein, is a material which has a strong affinity for water. Even more specifically, the material used herein is defined as hydrophilic by the geometry of water on a flat surface, specifically, the angle between a droplet's edge and the surface underneath it (contact angle). If the droplet spreads, wetting a large area of the surface, then the contact angle is less than 90 degrees and that surface is considered hydrophilic. In exemplary embodiments, the material is absorbent, wicking, cleanable, durable, dimensionally stable, and anti-pathogenic. Exemplary materials comprise cellulose-based materials. The material may be treated to render it hydrophilic, such as with an anionic-ethoxylated sulfonated polyester (AESP) and a high molecular weight ethoxylated polyester (HMWEP) to maximize its hydrophilicity. In optional embodiments, the material may be a fabric such as a polyester/cotton blend, nylon, corn fiber, or other fibers that are conducive to capillary action. The material may be a microdenier knitted fabric, but it may alternatively be an ordinary knitted fabric or a woven tufted or non-woven fabric, or a mesh. In optional embodiments, the material may comprise a metal mesh framework, a synthetic mesh framework, or a cable rope. The material may also be heat-resistant. The material may further be flecked with an antimicrobial agent, such as silver.

The material 126 may have pores or capillaries for the fluid to travel through via sorption and/or capillary action. In embodiments, it may use capillary action to convey fluid from the first chamber to the hydrophilic material 126 to the second chamber 118 where it is heated by heating element 124 to produce a vapor that rises though the second chamber 118. The heating element 124 may be positioned on a top side of the hydrophilic material 126. In other embodiments, the heating element 124 may surround the hydrophilic material 126 like a shroud. In other embodiments, such as that shown in FIG. 2, the heating element may have a smaller diameter than the hydrophilic material, and sit within the hydrophilic material.

The hydrophilic material 126 may be comprised of a single material throughout, or be comprises of a different material on the bottom portion than the middle or top portions, or the outer portion and the inner portion. In some embodiments, the hydrophilic material 126 may be tubular in shape, cubed, or be a strip. The fabric may also be bundled much like if one were to push a cloth down into a chamber. In an embodiment, hydrophilic material 126 is a tubular shaped member compressed in passage 128, leaving a small space between the bottom of the material 126 and the bottom internal portion of the housing. In this way, the material 126 fits snuggly in the passage 126 so that a seal is formed between edges of the material 126 and the first chamber 116, such that fluid flow will be through the pores through material 126 and not through any edge gaps exceeding the average pore. Consequently, the material 126 should be of appropriate pore size and material so that capillary action provides a supply of fluid 130 such that when heat is transferred from heating member 124 to material 126, the material 126 provides for a boiling transition from liquid to vapor/steam over an appropriate range of temperatures and pressures. Also, a vapor tight seal between due to compression between the material 126 the edges of 134 of the chambers. The space is configured to allow fluid to seep in and form a shallow fluid reserve for the fluid to seep in from the first chamber 116.

Figure 11:
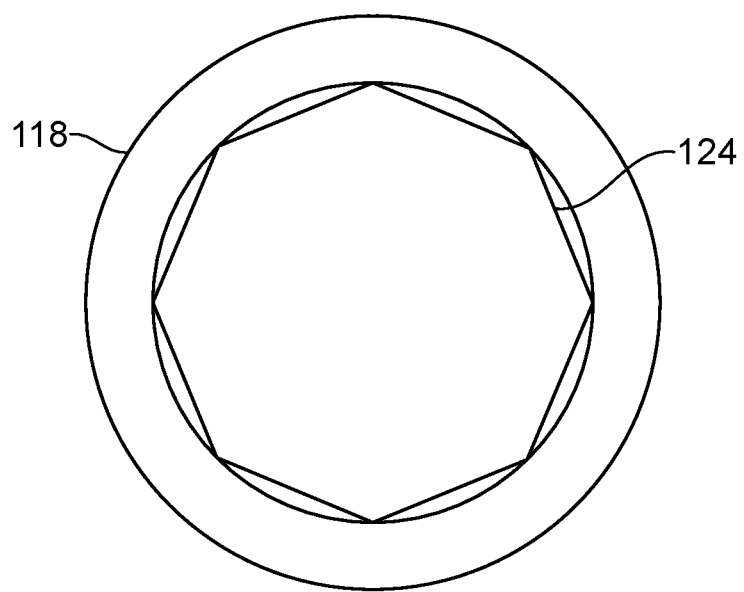
FIG. 11 is a top view of the device showing an optional embodiment or configuration of the heating element in accordance with embodiments of the present invention.

Referring still to FIG. 1, the heating element 124 is in electronic communication with and controlled by a printed circuit board (PCB) 132, which is configured to control the electrical elements of the device 100, and which will be discussed in greater detail with relation to FIG. 7. The heating element 124 is configured to heat fluid to form a vapor, the temperature of which will be between 0-115 degrees Fahrenheit and optimally operate between 100-115 degrees Fahrenheit +/−3 degrees. The temperature of the vapor/steam/mist is user controllable via a user interface or a toggle or switch that is shown in FIG. 4. The heating element 124 may be formed with heat conductive materials, such as metals, for conducting heat into the material hydrophilic material 126 for boiling the fluid. The heating element 124, in optional embodiments, may be formed with a series of narrow grooves or slots to increase the surface area of the heating element to speed up the conversation of fluid to vapor or steam. An optional or alternative configuration of the heating element is shown in FIG. 11.

With reference still to FIG. 1, a variable circulator 122 is positioned proximate the top 104 of the housing 102, positioned diagonal (e.g., approximately 45 degrees with respect to the bottom of the housing) to the steam flow and is communication with the PCB 132 and user interface (shown in FIG. 4) such that a user has variable control of the speed of the circulator 122. The circulator 122 may, in some embodiments, comprise a fan assembly having a rotor 136 and a plurality of vanes 138, the rotor 136 being adapted to be rotated by an electric motor (not shown). The fan motor is supported within a housing 102 by an orifice outlet 140. In this way, the user can control the temperature of the steam or vapor by increasing or decreasing the speed of the vanes of the circulator 122. In operation, a motor 142 is disposed of in the bottom 106 of the housing 102 in axial alignment with the housing 102 and is of sufficient power to rotate a drive shaft. Once rotating, the circulator, via pressure change in the second chamber, pulses the steam, vapor and mist from the second chamber 118 into the attachment member and eye cup, shown greater detail with relation to FIG. 3.

Optionally, a third chamber 120 may be provided to supply medication to the first chamber. In this embodiment, a valve 150 is disposed on the wall of the third chamber, and is controllable via UI. A second port 152 allows the user to pour or inject a medication to the third chamber. In operation, a user via the UI can mix a specified amount of the medication with the fluid (dH2O) to treat the eye or skin of the user.

Figure 2:
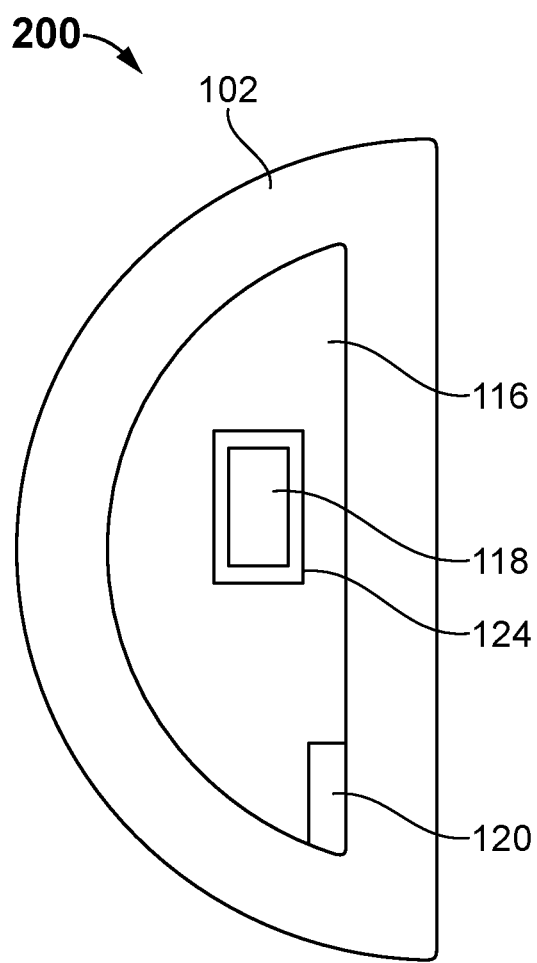
FIG. 2 is a bottom view of the device showing the chambers of the device in accordance with embodiments of the present invention.

Now with reference to FIG. 2, a bottom view of the device of FIG. 1 is shown generally at 200. FIG. 2 is provided to show the configuration, in an embodiment, of the housing 102, first chamber 116, second chamber 118, and the heating element 124. As can be seen in FIG. 2, the housing 102 envelopes the first chamber 116, which in turn envelopes the second chamber 118, and the heating element rests atop of the second chamber 118, while partially enveloping it on the sides down approximately twenty percent the length of the hydrophilic material, however, it may envelope the material anywhere from zero to ninety-five percent the material. The optional third chamber 120 is also shown therewith.

Figure 3:
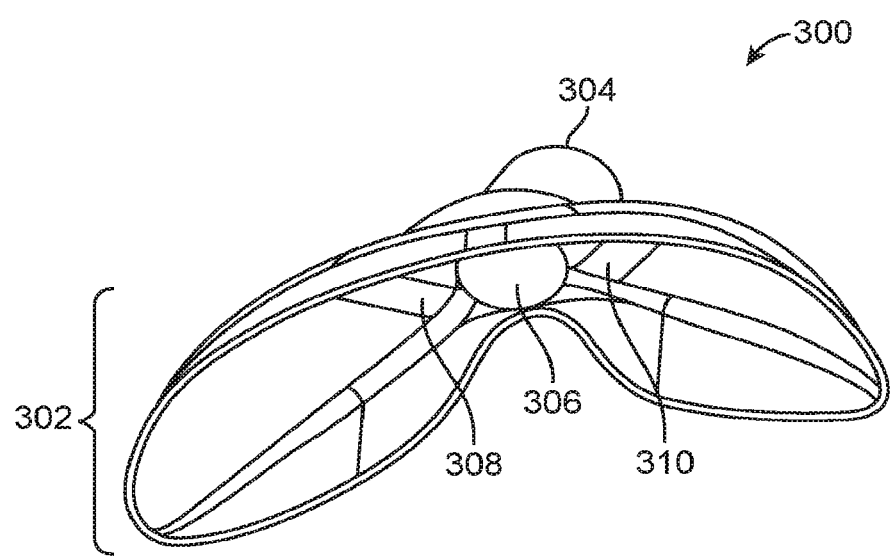
FIG. 3 is a perspective view of the eye member attachment in accordance with embodiments of the present invention.

With reference now to FIG. 3, an eye attachment member of the device of FIG. 1 is shown generally at 300. The eye attachment member 300 is configured to treat one eye or two eyes of the user, depending upon the attachment. It is connectable to the top side of the housing, and defines a vapor passage for directing the vapor from the second chamber to the eye of the user. The eye attachment member comprises eye cup 302, a neck portion 304, vapor passage 306, left routing channel 308, and right routing channel 310. In operation, the eye cup 302 is connected to the neck 304 at one end, and the neck is removabley attached to the housing on an opposite end. In optional embodiments, the neck is also removably attached to the eye cup to provide additional or different length necks which would be chosen by the user. In optional embodiments, the eye cup that covers both eyes of the user comprises a left routing channel 308 and a right routing channel 310, the channels configured to direct vapor towards the users right and left eye uniformly. The eye cup 302 may be formed of various materials, all materials being biocompatible materials that meet applicable requirements of ISO 10993 series of standards, for example medical grade silicone. The neck portion 304 may be made of the same materials as the eye cup 302, or a material that has a higher density or hardness if needed. Vents may be disposed therein as well.

Figure 5:
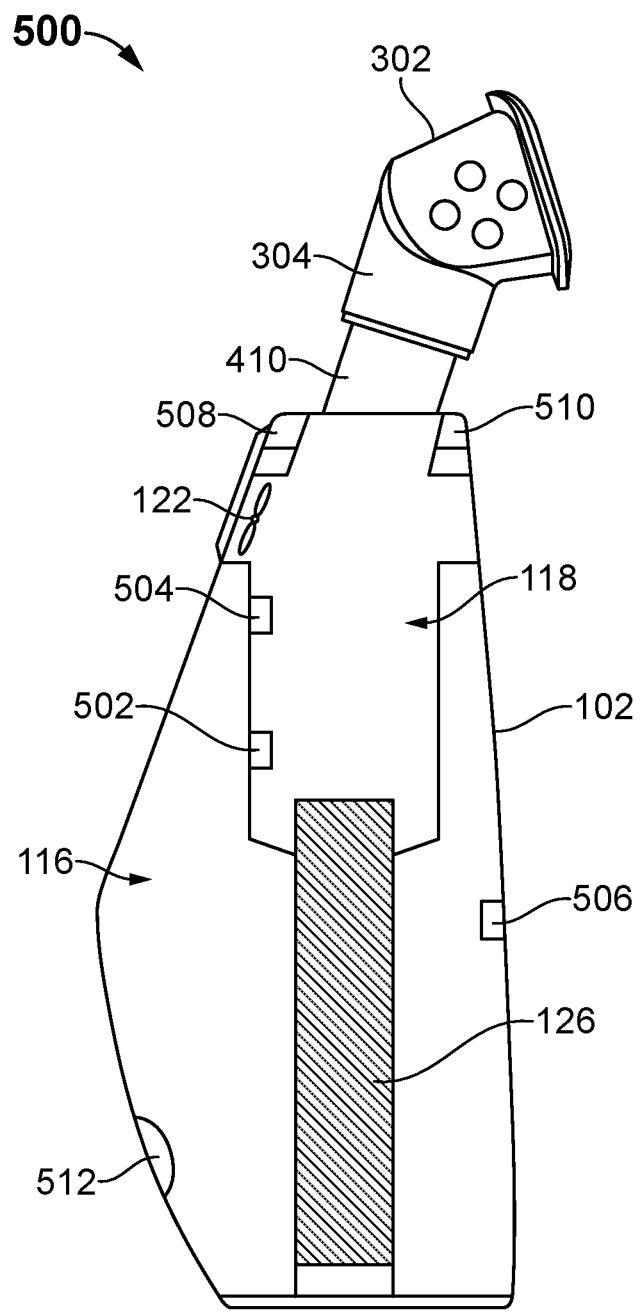
FIG. 5 is side view of the device in accordance with embodiments of the present invention.

With reference now to FIG. 4, a partially exploded view of the device of FIG. 1 is shown generally at 400. The device comprises eye cup 302, neck 304, housing 102. In this embodiment, the neck comprises a plurality of vents 402 disposed through the surface of the arm 410 and configured to regulate the temperature of the vapor and to regulate the amount of vapor that reaches the eye or eyes of the user. As stated with relation to FIG. 3, the neck portion 304 is removably attached to the arm via friction fit, and comprises a slit 412 configured to allow mating of the neck portion and an arm 410, and further comprises a second slit 408. It should be noted that while vents 402 are disposed through the arm portion 410, they may also be positioned on the neck 304 or eye cup 302 as shown in FIG. 5. Furthermore, while two-piece construction of the arm 410 and neck 304 is shown, it should be appreciated that the arm 410 and neck 304 may be one piece, and can be fit into the housing 102 in a similar fashion.

Still referring to FIG. 4 the, housing 102 further comprises a user interface positioned on the outside of the housing 102, the UI comprising an on/off switch 404 and buttons or toggles 406 which reference different modes. In optional embodiments, a single button that is pressure sensitive may be employed such that, in operation, the pressure-sensitive buttons 406 is in communication with the PCB and comprises a button (anyone of the buttons shown), configured for the thumb of the user such that as the toggle or button 406 is depressed, the PCB signals the variable circulator to increase a flow rate, thus decreasing the temperature. In optional embodiments, separate buttons each having been pre-set for different speeds may apply. Another mode or button that may be employed to activate at least light emitting diode ultraviolet germicidal irradiation (UVGI) configured to disinfection the fluid, the vapor, or both, using short wavelength ultraviolet (UV-C) light to kill or inactivate microorganisms, the UVIG being positioned in the first chamber, the second chamber, or both, as is shown in FIG. 5.

With reference to FIG. 5, a side view of the vapor device of FIGS. 1-3 is shown generally at 500. For purposes of perspective, a housing 102, the first chamber 116, second chamber 118, hydrophilic material 126, the variable circulator 122, and the eye cup 302. The PCB (shown in FIG. 1) is in communication with a plurality of components that are disposed both inside and outside the housing 102 and chambers 116 and 118 to ensure safe operation of the device, and for certain measures of convenience. The PCB is positioned on the flat side of the housing 102 together with the battery 128 (shown in FIG. 6). As shown, vents can be in the eye attachment member itself in optional embodiments.

A temperature sensor 502 is positioned in the second chamber communication with the PCB, a flow, at least a flow rate sensor 504 in the second chamber and communication with the PCB, and a timer 506 in communication with PCB 132, the timer being set in a to predetermined time range and configured to turn the device on and off once outside of the predetermined range The temperature sensor 502 and at least one flow rates sensor 504 are configured to turn the device off if predetermined parameters are exceeded. The temperature sensor is configured to ensure the temperate does not exceed 115 degrees Celsius, +/−3 degrees, and if it does, an automatic shutdown will occur. The device, in embodiments a minimum flow rate of 1.0 ml/min, and be controlled based on feedback from the sensor. In other embodiments, the flow rate may be between 0.1 ml/min and 3 ml/min.

Furthermore, the housing 102 may comprise a synovial joint 508 and 510 on which the arm 410 attached is capable of motion around an indefinite number of axes only bounded by the housing 102. In embodiments, the synovial joint and comprises a ball and socket positioned in an end of the housing. In this way, eye cup be adjusted relative to an eye by configuring eye cup such that device 100 can be pivoted about a point, and the user can comfortably use at many different angles.

The device further comprises light emitting diode ultraviolet germicidal irradiation (UVGI) 512 configured to disinfect the fluid, the vapor, or both, using short wavelength ultraviolet (UV-C) light to kill or inactivate microorganisms. The UVIG may be positioned in the first chamber, the second chamber, or both, as is shown in FIG. 5.

Figure 6:
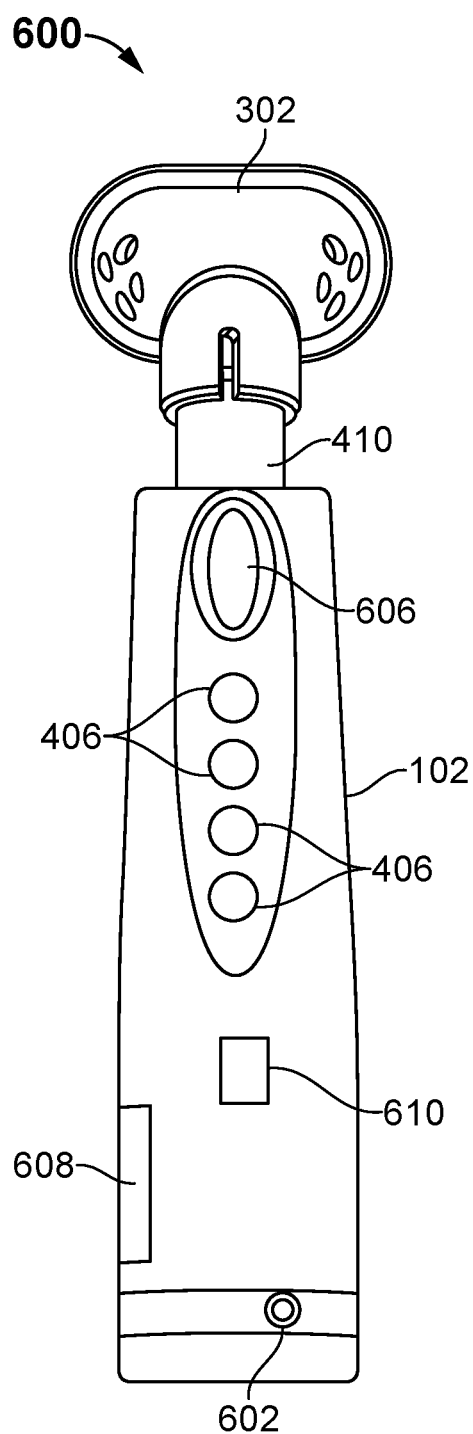
FIG. 6 is a back view of the device in accordance with embodiments of the present invention.

With reference now to FIG. 6, a back view of the device of FIG. 1 is shown generally at 600. For purposes of perspective, a housing 102 and the eye attachment cup 302 are shown together with the UI 406. The PCB 132 is in communication with a plurality of components that are disposed inside the housing 102 and chambers 116 and 118 to ensure safe operation of the device, and for certain measures of convenience.

The device further comprises a rechargeable battery in connection with the motor 608 and a charging port 602 provided by the housing, the battery being 3.7V. In optional embodiment, any type of battery may be used. The battery is in communication with motor 608, which operates the variable circulator of FIG. 1. Bluetooth may be incorporated as well via buttons 610, and be in communication with a mobile web application so that a user can control time settings, provide battery info, usage info (how often they have used it throughout the day) which can help their doctor's in measuring compliance. While Bluetooth® is used as an example, other protocol for wireless communication over short distances may be used as well using radio waves, IR, and the like. The Bluetooth may operate in the ISM bands at 2.4-5 GHz or above with a set of 79 hop carriers with 1 MHz spacing. A master-slave communication model with frequency hopping spread spectrum (FHSS) transmission technique is adopted in the Bluetooth specification to ensure protection from interference and security of data the user provides therein.

A fill port 606 is further provided, the fill port being disposed on the outside of the housing and configured to allow a user to easily fill the first chamber with fluid, typically dH2O. While the fill port is shown positioned near the top of the housing, the fill port may be in any useful location. In operation, the hand-held portable steamer device is fully adjustable, able to be controlled by in a myriad of different ways, be it mechanically or electrically. The device 100 has a temperature range of providing heat from 100-115 degrees in some embodiments. The attachment serves dual purposes in that it is configured to provide direct pressure to the affected area based on the tight seal. In a wireless setting, the dimmer may be optionally coupled to network interface which enables communication with an external devices such as a controller via communication channels, which may be implemented as a hardwired or wireless communications link using suitable conventional technologies. While these components are shown as being within the housing, they may also be disposed within the eye member of FIG. 3.

Figure 7:
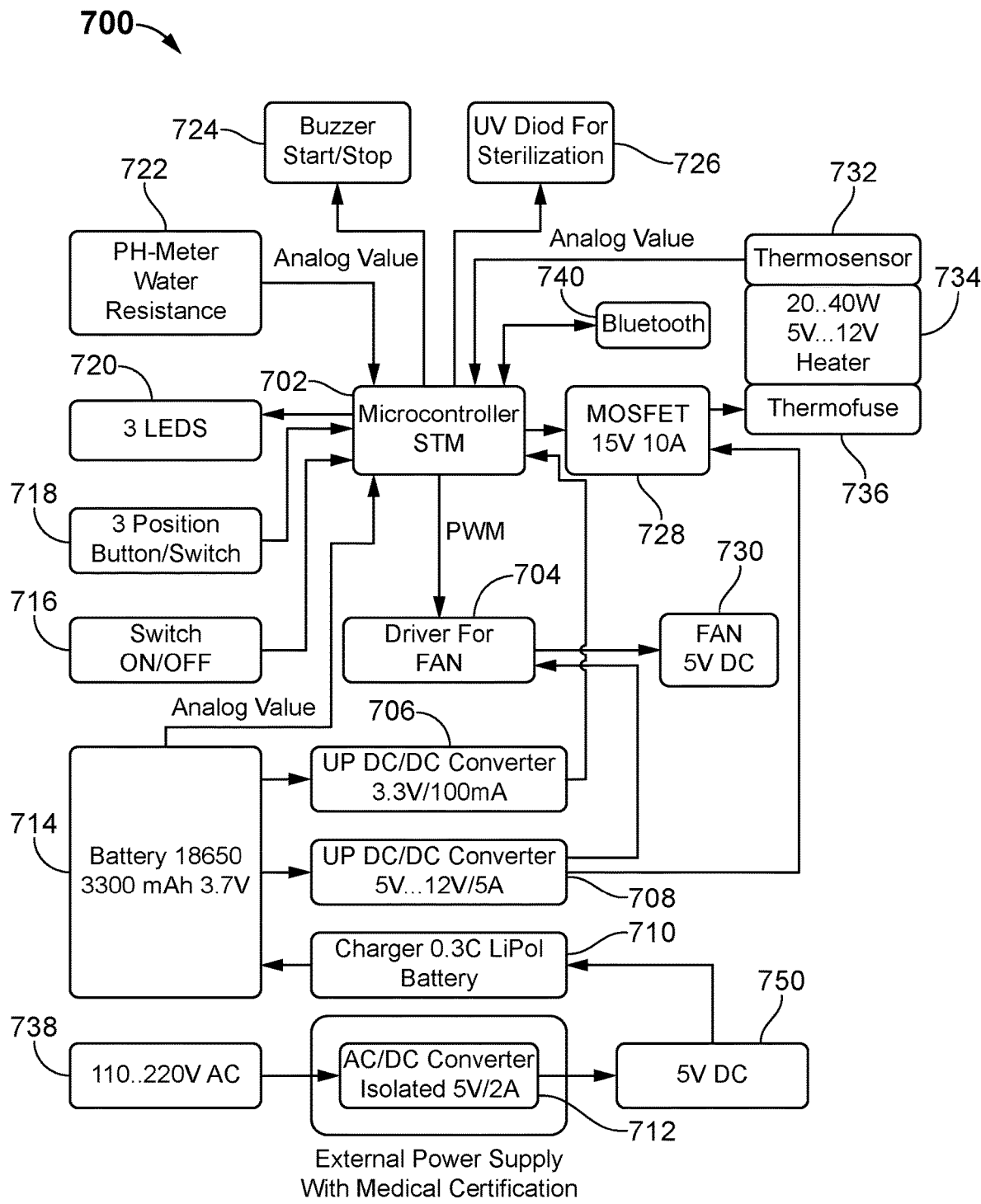
FIG. 7 is a block circuit diagram of the device in accordance with embodiments of the present invention.

With reference now to FIG. 7, a block diagram is provided showing some of the electrical and mechanical components that the device 100 comprises, as constructed according to one embodiment of the present invention as shown at reference numeral 700.

In this example, the microcontroller 702 is in communication with a plurality of components for which it controls. The microcontroller comprises one or more CPUs (processor cores) along with memory and programmable input/output peripherals. Program memory in the form of Ferroelectric RAM, NOR flash or OTP ROM is also often included on chip, as well as a small amount of RAM. Microcontrollers are designed for embedded applications, in contrast to the microprocessors used in personal computers or other general purpose applications consisting of various discrete chips.

In operation, power is drawn from an outlet (110v) 738, run through an AC/DC converter 712, to a charger 710, and housed in a battery 714. The battery 714 powers the microcontroller 702, which in turns controls the various electrical components of the device shown therein.

In embodiments, the microcontroller 702 is in communication with a driver 704 for the variable circulator 122 (e.g., fan). The fan 122 may run on five both direct current power block 730. A battery 714 is in electrical communication with the microcontroller 702 and DC/DC converters 706 and 708 are configured to provide power to the microcontroller and the various electrical and mechanical components of the invention. A charger 710 is in communication with an AC to DC converter 712, which is in communication with a wall outlet 738 (e.g., 110v) and 5V DC 750. An on/off switch is further provided at block 716 and is in communication with the microcontroller 702 and UI/toggle 718 is also in communication with microcontroller 702, as our lights 720 which are configured as an on/off indicator.

Still with reference to FIG. 7, the microcontroller 702 is in communication with the plurality of sensors, for example, PH sensor 722 thermo-sensors 732 and the like. UV diode for sterilization 726 is in further communication with microcontroller 702 as it is a start/stop mechanism 724. A heater 734 is in communication with both the thermosensor 732 and thermofuse 736.

A MOF SET 728 is in communication with the microcontroller 702 and battery 714 and is configured as a type of field-effect transistor (FET) with an insulated gate, whose voltage determines the conductivity of the device. This ability to change conductivity with the amount of applied voltage can be used for amplifying or switching electronic signals. A thermofuse 736 is in communication with MOF-SET 728.

Bluetooth® 740 is in further in communication with microcontroller 702, and is configured to connect to a user device via mobile application.

Figure 8:
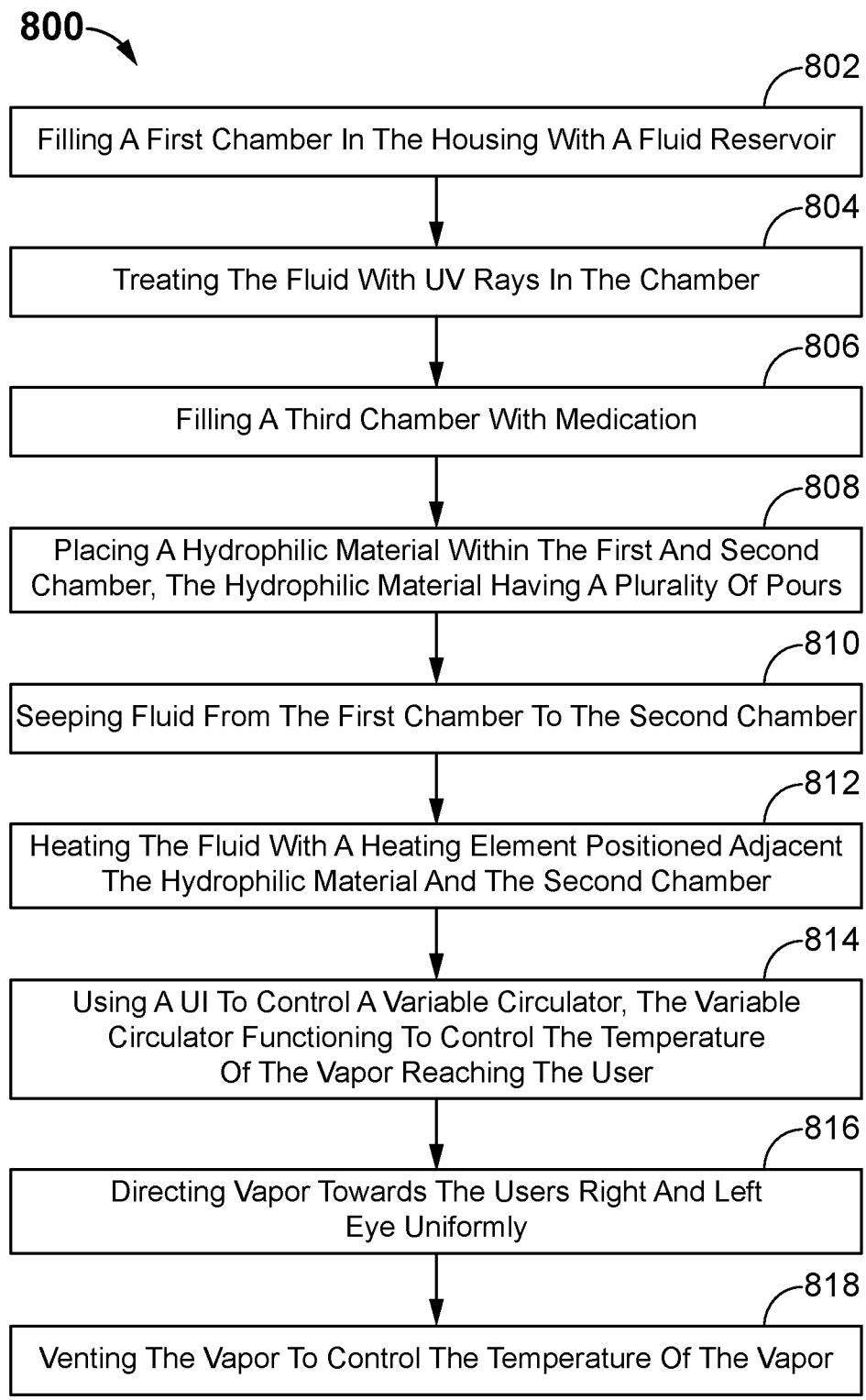
FIG. 8 is step-wise method flow chart of a method of using the device in accordance with embodiments of the present invention.

With reference now to FIG. 8, a stepwise method diagram is provided and shows the method of using the device herein at reference numeral 800.

Filling a first chamber in the housing with a fluid step 802 comprises using a fill port or a modular design to allow the user to easily fill the first chamber or fluid reservoir with dH2O.

Treating the fluid with UV rays in the chamber step 804 comprises comprising using at least light emitting diode Ultraviolet germicidal irradiation (UVGI) configured to disinfection the fluid, the vapor, or both, using short-wavelength ultraviolet (UV-C) light to kill or inactivate microorganisms, the UVIG being positioned in the first chamber, the second chamber, or both. In this way, the device can treat not only the fluid but the steam as well.

Filling a third chamber with medication step 806 comprises using a prescribed medication using a second port.

Placing a hydrophilic material within the passage, the hydrophilic material having a plurality of pours, step 808, comprises providing the hydrophilic material in the passage, the material being fully replaceable.

Seeping fluid from the first chamber to the hydrophilic material step 810 comprises using capillary action to draw fluid into the material Heating the fluid with a heating element positioned adjacent the hydrophilic material and the second chamber step 812 comprises heating the fluid to a boil to produce a steam and vapor.

Using a UI to control a variable circulator, the variable circulator functioning to control the temperature of the vapor reaching the user step 814 comprises providing buttons or levers to the user to control different modes provided therein.

Directing vapor towards the users right and left eye uniformly step 816 comprises providing an eye cup with passages that direct the vapor to each eye.

Venting the vapor to control the temperature of the vapor step 818 comprises providing vents in wither the eye cup, neck or arm.

Figure 9:
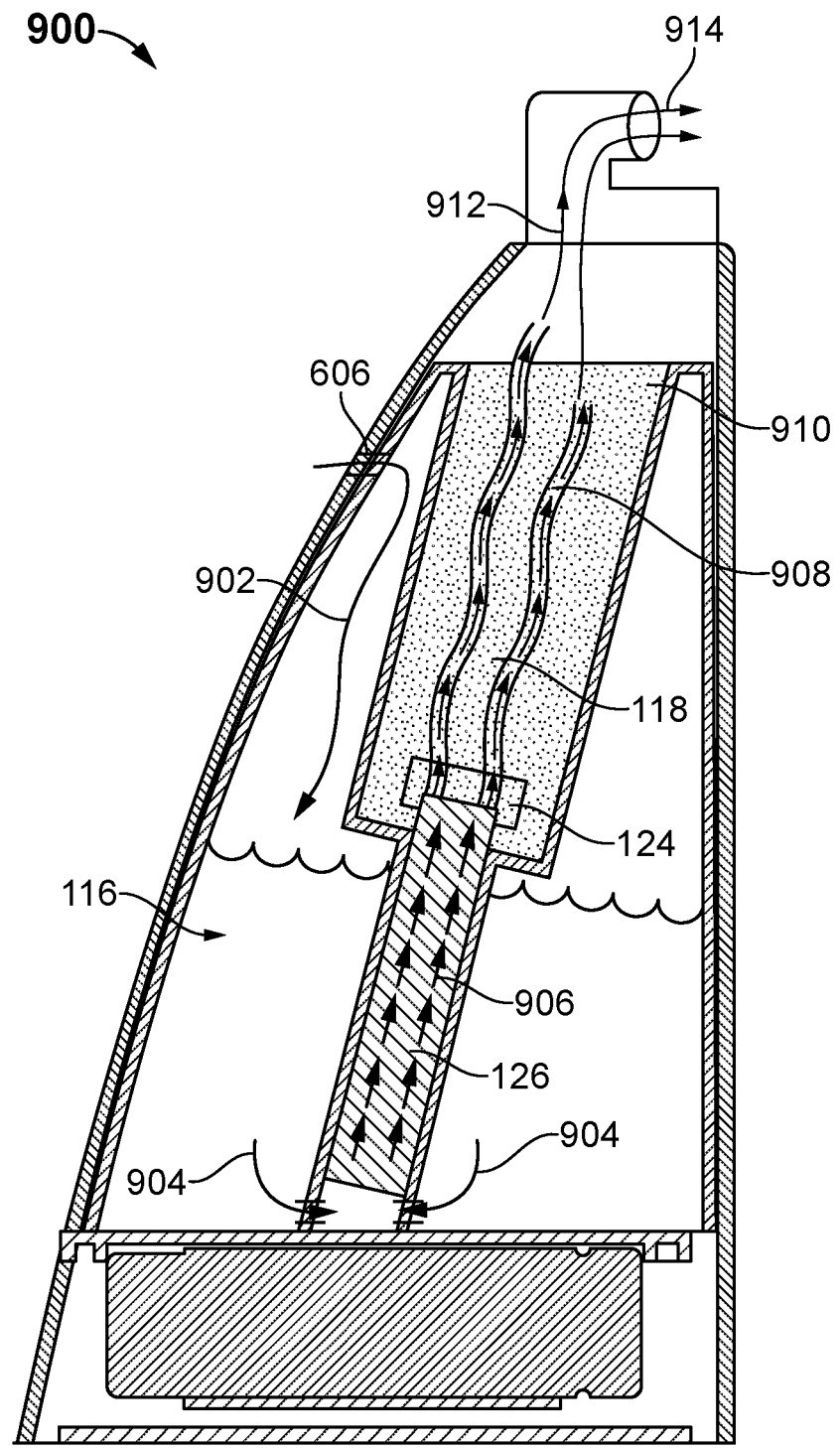
FIG. 9 is a cross-sectional view of fluid and steam flowing into the device in accordance with embodiments of the present invention.

FIG. 9 is a fluid flow diagram showing the fluid and steam flow of the device, shown generally 900. Arrow 902 denotes filling the first chamber 116 with a fluid, typically dH2O. The fluid then seeps into hydrophilic material 126 via passages 904. The heating element 124 heats the fluid moves up the material 126 via capillary action shown by arrows 906, where it is heated and turned into vapor/steam and aerosolized droplets in the second chamber 118, denoted by 908 and 912 respectively. The mixture then exits the device as shown via arrows 914.

Figure 10:
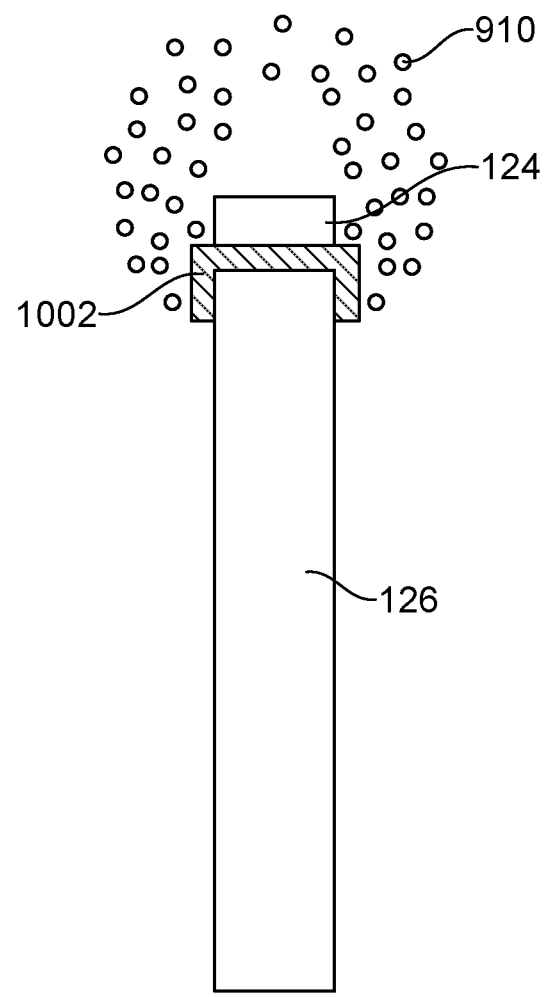
FIG. 10 is a partial side view of the interior of the housing in accordance with embodiments of the present invention.

With reference now to FIG. 10, the hydrophilic material 126 is shown together with a buffer 1002, which is formed of a perforated meal and is configured to protect the hydrophilic material 126 from the direct heat of the heating element 124. In operation, when heating element 124 is on, the aerosolized droplets can be seen at 910.

With reference now to FIG. 11, in optional embodiments, the heating element 124 has a diameter that is less than that of the hydrophilic material 126. Also, the heating element 124 is heptagonal to lower energy requirements. In this way, the hydrophilic material 126 surrounds the heating element.

While the present invention has been described in connection with what are presently considered to be the most practical and preferred embodiments, it is to be understood that the present invention is not limited to these herein disclosed embodiments. Rather, the present invention is intended to cover all of the various modifications and equivalent arrangements included within the spirit and scope of the appended claims.

Although specific features of various embodiments of the invention may be shown in some drawings and not in others, this is for convenience only. In accordance with the principles of the invention, the feature(s) of one drawing may be combined with any or all of the features in any of the other drawings. The words "including", "comprising", "having", and "with" as used herein are to be interpreted broadly and comprehensively and are not limited to any physical interconnection. Moreover, any embodiments disclosed herein are not to be interpreted as the only possible embodiments. Rather, modifications and other embodiments are intended to be included within the scope of the appended claims.

We claim:

1. A handheld device for treating an eyelid of a user, the device comprising:
    a housing having a bottom, a top, a side wall and a diagonal wall with an inner surface that faces diagonally toward the bottom of the housing;
    a fluid reservoir within and extending up from the bottom of the housing;
    a vapor reservoir located in the housing and having an opening in the top of the housing, wherein the vapor reservoir is positioned at least partially above the fluid reservoir, and wherein the inner surface of the diagonal wall of the housing comprises a wall of the vapor reservoir;
    a hydrophilic material extending from the fluid reservoir to the vapor reservoir, the hydrophilic material having a plurality of pores;
    a heating element positioned in the vapor reservoir, adjacent the hydrophilic material, wherein the heating element converts fluid absorbed into the hydrophilic material from the fluid reservoir to a vapor in the vapor reservoir and regulates a vapor temperature of the vapor inside the vapor reservoir;
    a printed circuit board (PCB) in the housing;
    a user interface disposed on an outside of the housing and in communication with the PCB;
    a variable circulator attached to the inner surface of the diagonal wall of the housing, within the vapor reservoir, wherein the variable circulator is in communication with the PCB and is angled diagonally toward the bottom of the housing, and wherein the variable circulator controls a flow of the vapor out of the opening in the top of the housing;
    a temperature sensor positioned in the vapor reservoir; and
    a tubular attachment removably coupled with the top of the housing, over the opening, to direct the vapor from the top of the housing toward the eyelid, wherein the tubular attachment comprises an eye cup disposed on an end of the tubular attachment for fitting over the eyelid of the user, wherein the PCB controls a speed of the variable circulator to automatically regulate the vapor temperature.

2. The device of claim 1, wherein the eye cup comprises:
at least a first vent disposed through a surface of the eye cup to further regulate the vapor temperature; and
a hollow neck portion on a bottom end of the eye cup,
wherein the eye cup is removably attached to the end of the tubular attachment via friction fit, and
wherein the neck portion comprises a slit for mating the neck portion with the end of the tubular attachment.

3. The device of claim 1, wherein the tubular attachment is connected to a ball and socket joint positioned at the top of the housing.

4. The device of claim 1, further comprising:
a power switch on the outside of the housing and in electronic communication with the PCB;
a flow rate sensor in the vapor reservoir and coupled with the PCB; and
a timer in communication with the PCB that turns the handheld device on and off automatically at preset times.

5. The device of claim 1, further comprising:
a motor in communication with the PCB that when actuated powers the variable circulator; and
a rechargeable battery in connection with the motor and in connection with a charging port provided in the housing.

6. The device of claim 1, further comprising a fill port on the housing, for accepting the fluid.

7. The device of claim 1, further comprising an antimicrobial agent coupled with the hydrophilic material.

8. The device of claim 1, further comprising at least one light emitting diode positioned in the vapor reservoir and configured to emit short-wavelength ultraviolet light to kill or inactivate microorganisms in the vapor.

9. The device of claim 1, further comprising a medicated compound reservoir in fluid communication with the hydrophilic material via a pathway having a valve, such that the user has the ability to inject a medicated compound into the medicated compound reservoir which flows into the fluid reservoir for vaporization.

10. The device of claim 1, further comprising a perforated metal buffer positioned between the heating element and the hydrophilic material, the heating element being positioned at a top of the hydrophilic material.

11. A method for treating an eyelid of a user, the method comprising:
adding fluid to a fluid reservoir in a housing of a handheld device;
attaching a tubular attachment to a top of the housing, over an opening in the housing;
placing a first end of a hydrophilic material in the fluid in the fluid reservoir, such that a second end of the hydrophilic material is located above the first end, in a vapor reservoir of the handheld housing, wherein the hydrophilic material comprises a plurality of pores;
allowing the fluid to travel up the hydrophilic material from the first end to the second end;
heating the fluid in the hydrophilic material within the vapor reservoir with a heating element positioned in the vapor reservoir, adjacent the second end of the hydrophilic material, to convert the fluid to a vapor;
regulating a vapor temperature in the vapor reservoir by adjusting the heating element;
activating a variable circulator located on a diagonal wall of the vapor reservoir to move the vapor in a direction toward a bottom of the handheld housing;
sensing the vapor temperature using a temperature sensor positioned in the vapor reservoir;
automatically controlling a speed of the variable circulator, based on the sensed vapor temperature, using a printed circuit board (PCB) coupled with the variable circulator; and
placing an eye cup attached to an end of the tubular attachment over the eyelid of the user, to direct the vapor to the eyelid of the user.

12. The method of claim 11, further comprising:
attaching the eye cup to the end of the tubular attachment, wherein the eye cup is sized to fit over both eyes of the user, and wherein directing the vapor comprises directing the vapor towards the user's right eye and the user's left eye uniformly.

13. The method of claim 11, further comprising venting a portion of the vapor through multiple vents in least one of the eye cup or the tubular attachment, wherein the eye cup is removably attached to the tubular attachment via friction fit.

14. The method of claim 11, further comprising adjusting the tubular attachment relative to the handheld housing via a ball and socket joint connecting the tubular attachment to the handheld housing.

15. The method of claim 11, further comprising receiving a user input from the user via a user interface on the handheld housing to adjust a treatment setting, wherein the user interface is coupled with the PCB.

16. The method of claim 11, further comprising recharging a battery located inside the handheld housing and used to power at least the variable circulator, wherein the handheld housing comprises a charging port for recharging the battery.

17. The method of claim 11, further comprising
emitting short-wavelength ultraviolet light from at least one light emitting diode located in the vapor reservoir, to kill or inactivate microorganisms in the vapor.

* * * * *